United States Patent
Banes

(10) Patent No.: US 6,218,178 B1
(45) Date of Patent: Apr. 17, 2001

(54) LOADING STATION ASSEMBLY

(75) Inventor: Albert J. Banes, Hillsborough, NC (US)

(73) Assignee: Flexcell International Corporation, McKeesport, PA (US)

( * ) Notice: Subject to any disclaimer, the term of this patent is extended or adjusted under 35 U.S.C. 154(b) by 0 days.

(21) Appl. No.: 09/306,109

(22) Filed: May 6, 1999

Related U.S. Application Data

(60) Provisional application No. 60/084,728, filed on May 8, 1998.

(51) Int. Cl.$^7$ ................................................. C12M 3/00

(52) U.S. Cl. ........................... 435/305.1; 435/305.2; 435/809

(58) Field of Search .................... 435/284.1, 286.1, 435/286.5, 286.6, 286.7, 288.3–288.5, 288.7, 297.5, 305.1–305.4, 303.1, 303.3, 809

(56) References Cited

U.S. PATENT DOCUMENTS

| | | | |
|---|---|---|---|
| 4,087,327 | 5/1978 | Feder et al. | 195/1.7 |
| 4,623,355 | 11/1986 | Sawruk | 623/66 |
| 4,642,220 | 2/1987 | Björkman | 422/101 |
| 4,695,547 | 9/1987 | Hilliard et al. | 435/173 |
| 4,735,778 | 4/1988 | Maruyama et al. | 422/102 |
| 4,839,280 | 6/1989 | Banes | 435/285 |
| 4,851,354 * | 7/1989 | Winstion et al. | 435/284 |
| 4,940,853 | 7/1990 | Vandenburgh | 435/240.23 |
| 5,348,879 * | 9/1994 | Shapiro et al. | 435/240.241 |
| 6,037,141 * | 3/2000 | Banes | 435/30 |
| 6,048,723 * | 4/2000 | Banes | 435/305.1 |

FOREIGN PATENT DOCUMENTS 2155948   10/1985   (GB) ............. C12M/1/18

OTHER PUBLICATIONS

Lee et al. 'An equibiaxial strain system for cultured cells.' Am. J. Physiol. vol. 271 (1996), pp. C1400–C1408.*

Leung et al., "Cyclic Stretching Stimulates Synthesis of Matrix Components by Arterial Smooth Muscle Cells in vitro", Science, vol. 191, Feb. 6, 1976, pp. 475–477.

Brunette, "Mechanical Strectching Increases the Number of Epithelial Cells Synthesizing DNA in Culture", J. Cell Sci. 69, 35–45 (1984).

Somjen et al., "Bone Remodelling Induced by Physical Stress is Prostaglandin $E_2$ Mediated", Biochimica et Biophysica Acta, 627 (1980) 91–100.

Banes et al., "A New Vacuum–Operated Stress–Providing Instrument That Applies Static or Variable Duration Cyclic Tension or Compression to Cells In Vitro", J. Cell Sci. 75 (1985) pp. 1–8.

Leung et al., "A New In Vitro System for Studying Cell Response to Mechanical Stimulation", Exp. Cell Res. 109 (1977), pp. 285–298.

Winston et al., "The In Vitro Response of Endothelium to Mechanical Loading", 38th ACEMB 1985, p. 88.

Winston et al., "Response of Endothelial Cells in Culture to Biaxial Deformation", Northeast Bioengineering Conference, University of Pennsylavnia, 1987, 2 pp.

Thibault et al., "Mechanical Characterization of Membrane-like Biological Tissue", J. Biomechanical Engr., 1982, pp. 1–8.

* cited by examiner

Primary Examiner—William H. Beisner

(57) ABSTRACT

A loading station assembly for at least partially supporting the underside of a flexible cell membrane positioned in the bottom of a cell culture well. The assembly includes a planar member having a plurality of apertures. Each aperture receives a post having a flange which supports the membrane. A central opening defined in the planar member allows a vacuum to be drawn therethrough and to pull a portion of the membrane downwardly and cause a central portion of the membrane to stretch across the flange. Cells cultured on the membrane are subjected to a corresponding strain.

22 Claims, 7 Drawing Sheets

LOADING STATION ASSEMBLY

RELATED APPLICATIONS

This application claims the benefit of U.S. Provisional Patent Application Serial No. 60/084,728, filed May 8, 1998 entitled "Loading Post Assembly".

BACKGROUND OF THE INVENTION

1. Field of the Invention

The present invention relates to an assembly positionable beneath a flexible cell culture substrate membrane that supports the membrane and allows the membrane to stretch across the assembly equally in all directions when vacuum is applied at the periphery of the membrane thereby imparting equibiaxial strain to the growth surface of the membrane and to a cell culture apparatus incorporating the assembly. Alternatively, other geometries of the assembly can be employed that yield uniaxial or gradient strain in the membrane.

2. Prior Art

Elastomeric substrates have been used as surfaces for culturing cells in vitro. These substrates are usually treated to make them hydrophilic and are preferably bonded with matrix proteins. This development arose from the desire to flex cell cultures in vitro instead of culturing cells in a static environment such as exists in conventional cell culture devices. In particular, when cell cultures are grown on membranes which are flexed, the cells are strained and stressed which simulates a dynamic in vivo environment. Stressing of cells causes dramatic morphologic changes and biomechanical responses in the cells which are both long term and short term. Cell culture devices using an elastomeric substrate or a flexible cell culture membrane are flexed or stretched to induce mechanical stress and strain on the cells adhering thereto.

Such flexible cell culture membranes have been incorporated in devices by the Applicant including the single well and multi-well cell culture plates and devices disclosed in U.S. Pat. No. 4,789,601 which is incorporated herein by reference. The wells of this cell culture plate have a floor made from a flexible membrane which is treated to enable cells to adhere and grow thereon. Typically, negative pressure, from a vacuum, is applied to the underside of the cell culture plate to deform downwardly the flexible membranes in the wells of the culture plate.

An improved device is the subject of Applicant's copending U.S. patent application Ser. No. 09/201,570, filed Nov. 30, 1998 entitled "Culture Plate for Applying Mechanical Load to Cell Cultures", which is incorporated herein by reference. The device disclosed in the '570 application is similar to that of the device in the '601 patent in that it includes a multi-well culture plate having flexible cell culture membranes as the floors of the wells which may be subjected to negative pressure to downwardly flex the membrane. However, the membrane in the device in the '570 application is fixed between a base and a body so that either positive or negative pressure may be applied thereto causing upward or downward flexing of the membrane. The pressure differential applied to either of these devices may be released and reapplied to repeatedly apply stress and strain to the cells, thereby mimicking the mechanical load experienced by cells in mechanically active tissues such as the heart, lungs, skeletal muscles, bone, ligament, tendon, cartilage and the like. In this manner, the biological or biochemical responses of cells subjected to a flexed environment may be tested and studied.

However, certain cells normally experience equibiaxial strain in the plane of the cell. By equibiaxial it is meant that the strain is applied equally along both the x-axis and y-axis of the plane of the cell. In some applications of membrane stretching induced by either positive or negative pressure where the membrane is not supported, the cell culture membrane becomes arcuately shaped upon application of a differential pressure to the device. Such arcuate flexing renders difficult an analysis of the biologic responses of the cells since the strain varies in both the circumferential and radial directions. The impact of uniaxial strain in the plane of a cell (a strain in one of the x-axis or y-axis) is likewise important and difficult to analyze.

Accordingly, a need remains for a device for use with a cell culture plate with flexible cell culture membrane wells which provides for well-defined strain to be imposed on cells cultured thereon, wherein the strain is applied equibiaxially, uniaxially or in other defined strain field directions.

SUMMARY OF THE INVENTION

This need is met by the loading station assembly of the present invention. The loading station assembly is designed to allow equibiaxial, uniaxial or other directional stretching of a flexible cell culture membrane. In equibiaxial stretching the membrane is maintained in a generally planar configuration while strain is applied equally in both the radial and circumferential directions or in one direction only. The assembly includes a planar member and at least one post extending from a surface of the planar member. An upper surface of each post is adapted to support the flexible cell culture membrane. The planar member defines at least one aperture and each post is removably received within one of the apertures such that when one of the posts is removed, the membrane is not restricted from flexing downwardly at the position of the absent post. Each post includes a body receivable within one of the apertures and a flange having the upper surface, wherein the flange is positionable against the planar member surface.

The upper surface may be configured to allow equibiaxial, uniaxial or other directional stretching of a membrane. For equibiaxial stretching, the upper surface is preferably circular in shape. For uniaxially stretching, the upper surface preferably has a length which is longer than its width. The upper surface may be formed in a horizontal plane or in a plurality of planes. The planar member also defines a passageway adapted to allow fluid to flow through from one side of the planar member to an opposite side of the planar member such that a pressure differential may be applied to the underside of the membrane.

The present invention further includes a cell culture plate assembly having a cell culture plate defining at least one opening and a flexible cell culture membrane covering the opening. A loading station assembly is positioned adjacent the cell culture plate. The loading station assembly includes a planar member and at least one post extending from a surface of the planar member. An upper surface of each post supports a portion of the flexible membrane covering the opening. The planar member defines at least one aperture and the post is removably received within one of the apertures such that when one of the posts is removed, the cell culture membrane covering an opening is not restricted from flexing downwardly. Each post includes a body receivable within one of the apertures and a flange including the upper surface. The flange is positionable against the planar member. The flange upper surface may be formed in a horizontal plane or in a plurality of planes.

Preferably, each of the flexible member and the loading station assembly is made from a transparent material. In one embodiment of the invention, the post upper surface supports all of the flexible membrane covering the opening. The upper surface may be configured to allow equibiaxial, uniaxial or other directional stretching of the membrane. For equibiaxial stretching, the upper surface of the flange is preferably circular in shape. For uniaxially stretching, the upper surface of the flange preferably has a dimension which is approximately equal to a dimension of the membrane. More preferably, the opening in the cell culture plate is circular and the length of the upper surface is approximately equal to the diameter of the opening and the width of the upper surface is less than the diameter of the opening.

The planar member also defines a passageway adapted to allow fluid to flow from one side of the planar member to an opposite side of the planar member.

A complete understanding of the invention will be obtained from the following description when taken in accordance with the accompanying drawing figures wherein like reference characters identify like parts throughout.

BRIEF DESCRIPTION OF THE DRAWINGS

in FIG. 9;

DESCRIPTION OF THE PREFERRED EMBODIMENTS

Figure 3:
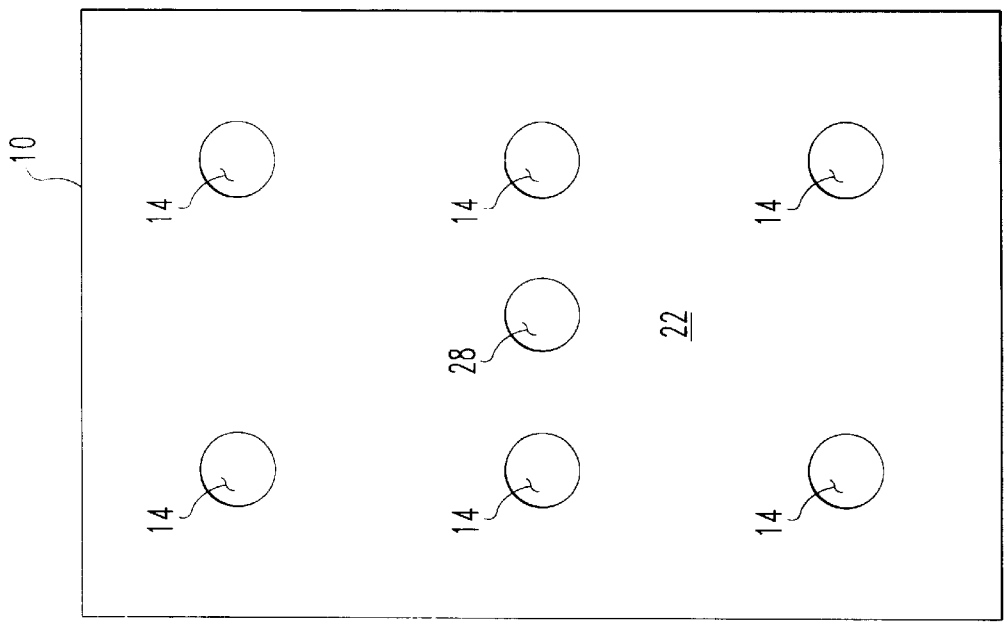
FIG. 3 is a plan view of the planar member depicted in FIG. 1.
Figure 1:
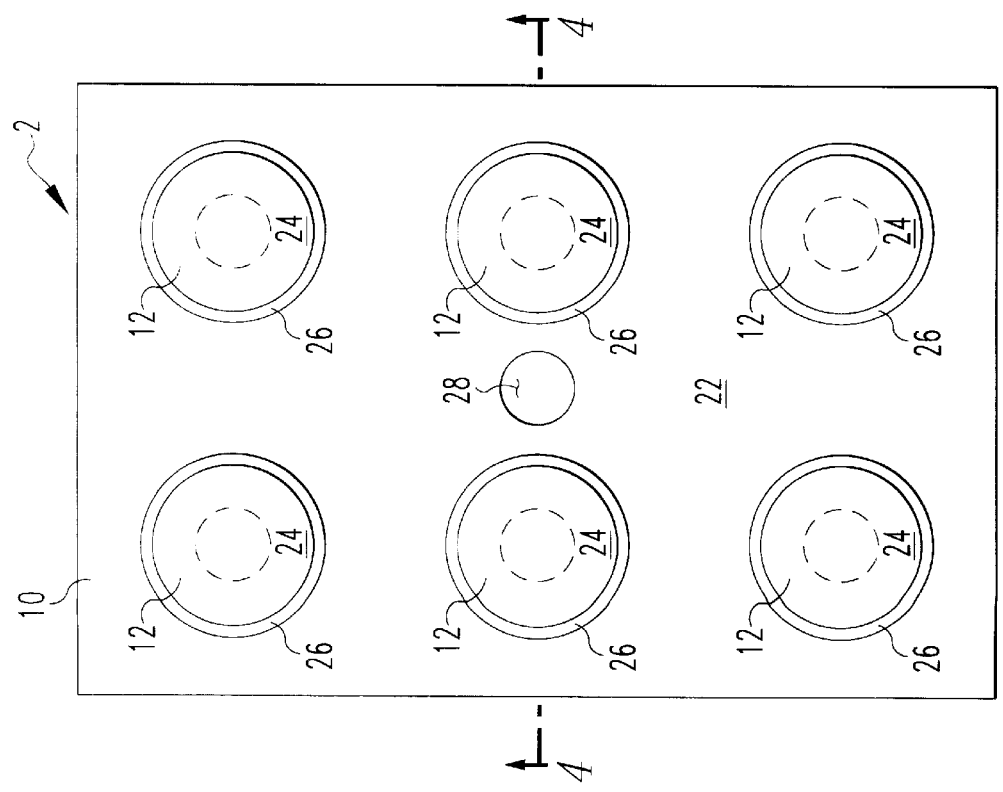
FIG. 1 is a plan view of a loading station assembly with a loading post and a planar member made in accordance with the present invention.
Figure 2:
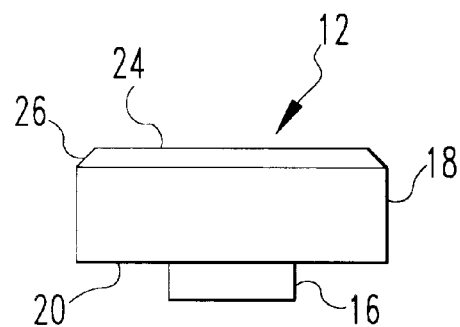
FIG. 2 is a side elevation view of the loading post depicted in FIG. 1.
Figure 4:
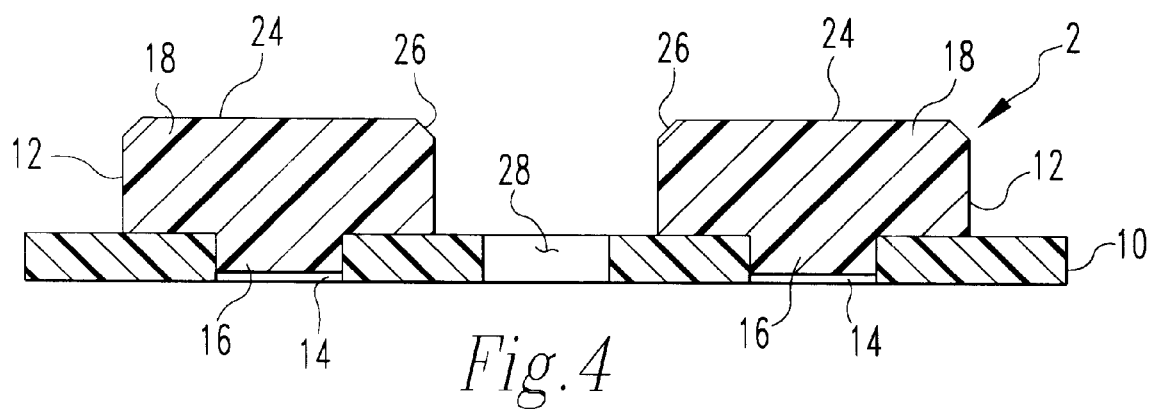
FIG. 4 is a cross sectional view of the loading station assembly shown in FIG. 1 taken along line 4—4.
Figure 5:
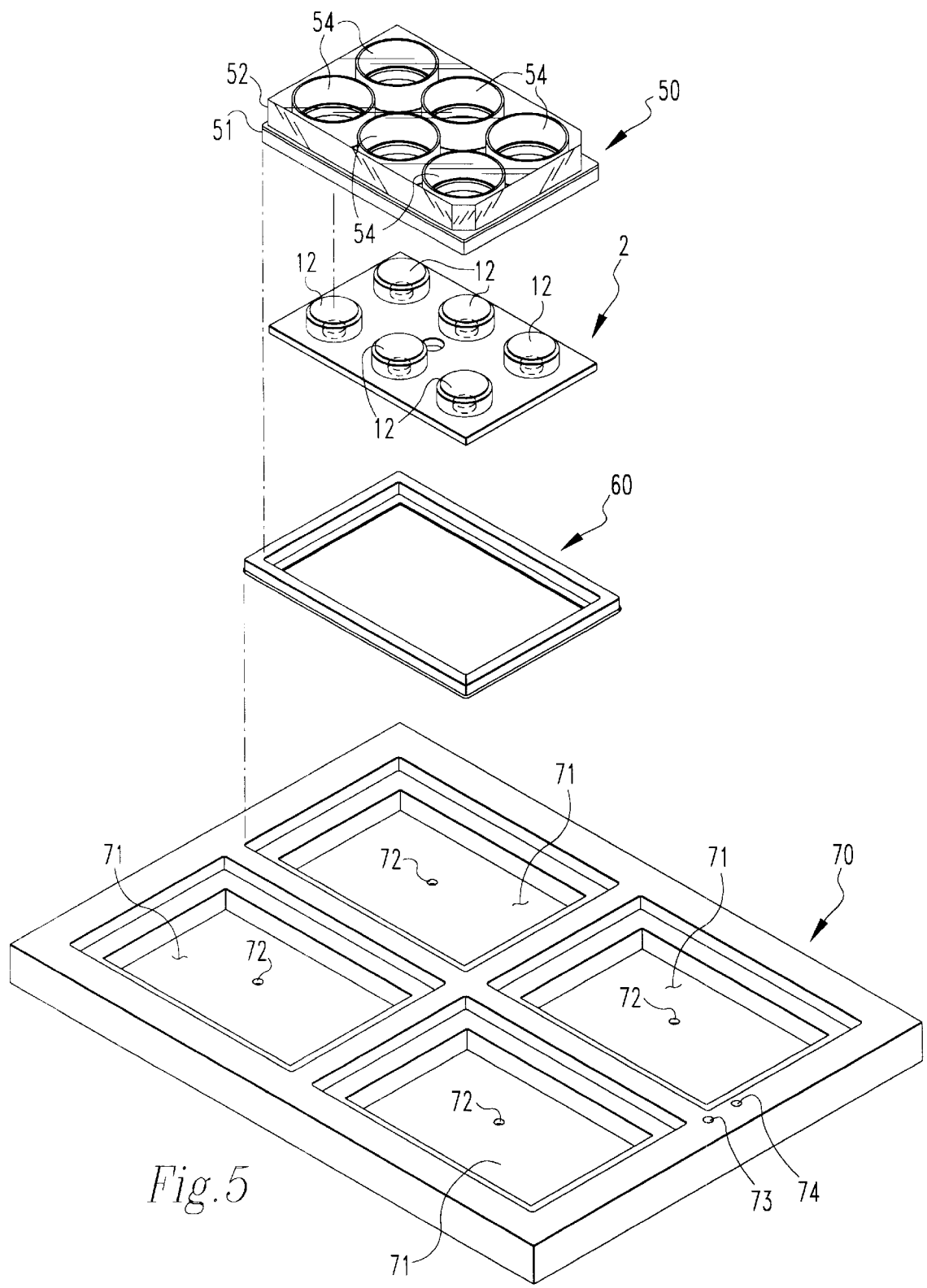
FIG. 5 is an exploded perspective view of the loading station assembly shown in FIG. 1 in use with a cell culture plate with a membrane, a gasket and a cell culture base plate.
Figure 6:
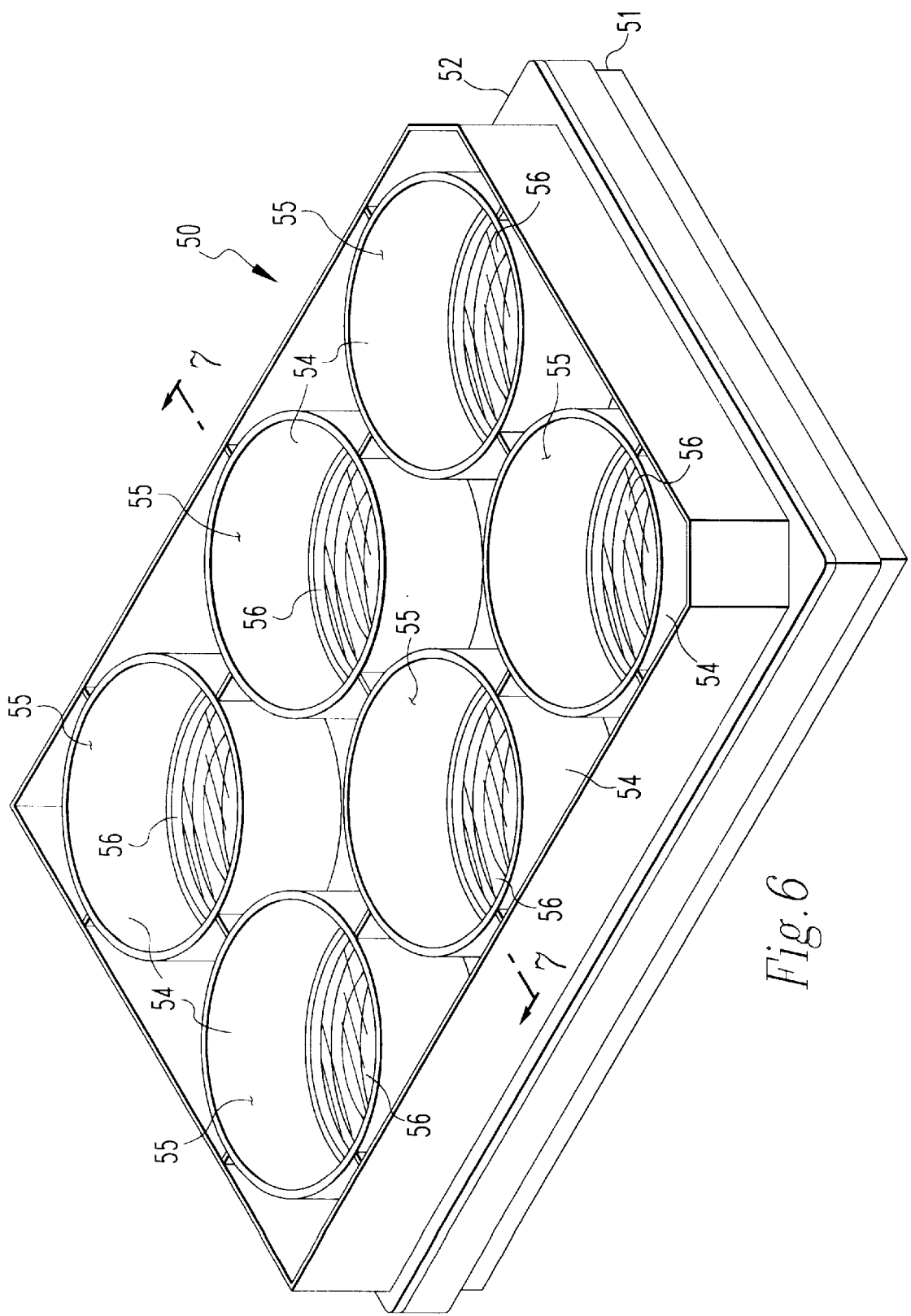
FIG. 6 is a perspective view of the cell culture plate shown in FIG. 5.

For purposes of the description hereinafter, the terms "upper", "lower", "right", "left", "vertical", "horizontal", "top", "bottom" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The loading station assembly of the present invention is designed for use with a multi-well cell culture plate wherein the floors of the wells are formed from a flexible material. Suitable multi-well cell culture plates are those disclosed in U.S. Pat. No. 4,789,601 and U.S. patent application Ser. No. 09/201,570. For convenience, the loading station assembly is described hereinafter as used with the devices disclosed in the '570 application, and this is only meant to be exemplary. It should be understood that the loading station assembly may be used with other multi-well cell culture plates having flexible-bottom wells which are not specifically described herein. It should be understood that the loading station assembly also may be used with single well cell culture plates or devices having flexible-bottom wells.

As shown in FIGS. 1–4, one embodiment of the loading station assembly 2 of the present invention includes a planar member 10 having a plurality of loading posts 12 extending therefrom. The planar member 10 defines a plurality of spaced apart apertures 14. The loading posts 12 each include a column 16 which is releasably fitted into one of the apertures 14. A head or flange 18 integral with the column 16 has a lower surface 20 which seats onto an upper surface 22 of the planar member 10. An upper surface 24 of the flange 18 is adapted to contact a flexible cell culture membrane as described in detail below and preferably is chamfered as indicated at reference numeral 26.

Preferably, the planar member 10 defines six apertures 14 which each receive a column 16. The number of apertures 14 may vary and is selected to match the number of wells in a multi-well cell culture plate having flexible-bottom wells.

The planar member 10 also defines a central opening 28 which is adapted to allow fluid flow from one side of the planar member 10 to an opposite side of the planar member 10. By the term fluid it is meant a gas (such as air) or a liquid. In particular, the space above the upper surface 22 of the planar member 10 may be evacuated through the central opening 28 when negative pressure is applied from below to the underside of the planar member 10 as described in further detail below.

Figure 7:
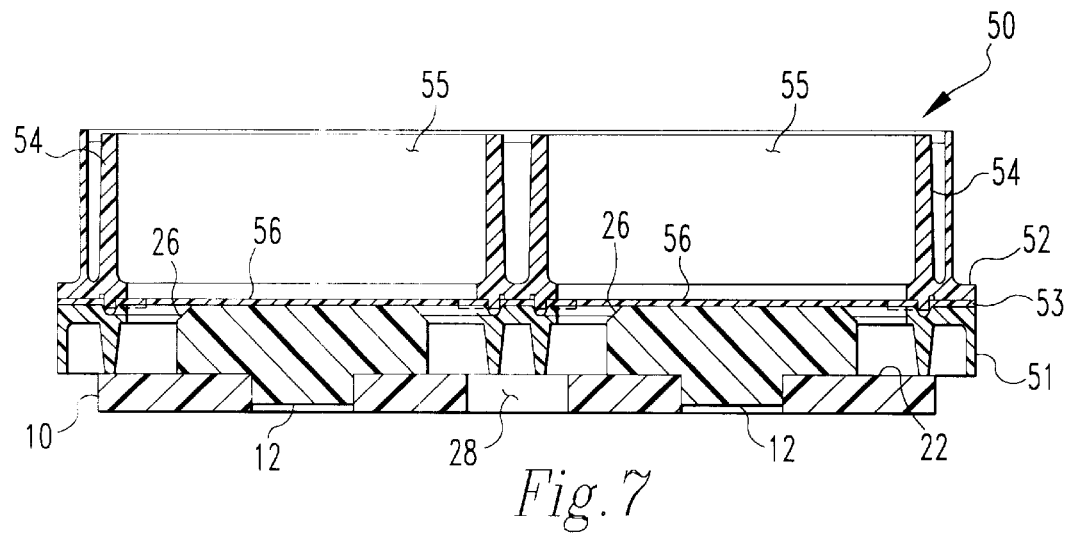
FIG. 7 is a cross sectional view of the cell culture plate shown in FIG. 6 taken along line 7—7 in relationship with the loading station assembly.
Figure 8:
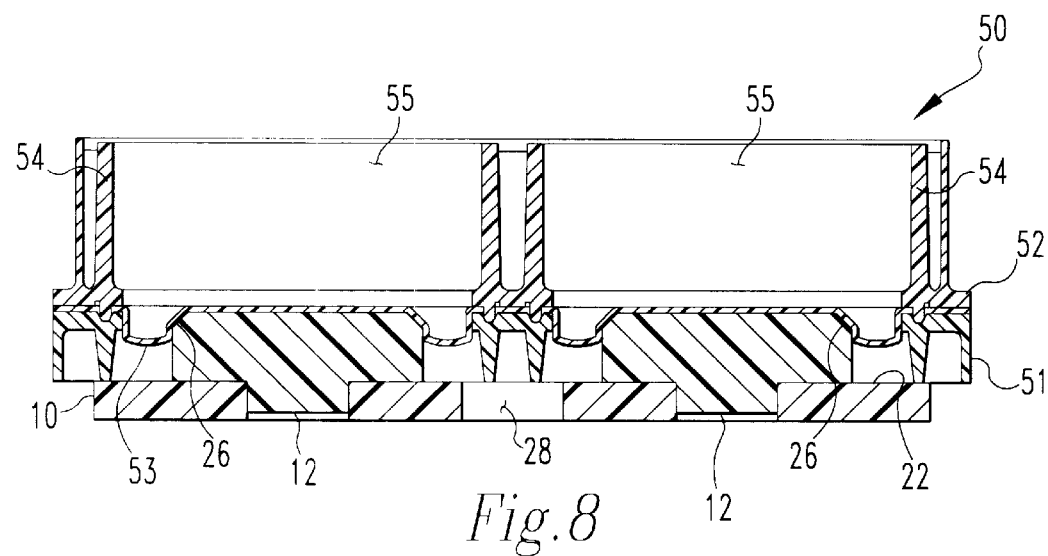
FIG. 8 shows the loading station assembly with cell culture plate shown in FIG. 7 upon application of negative pressure to the underside of the membrane.

As shown by example in FIGS. 5–8, the loading station assembly 2 is sized and configured for use with a multi-well culture plate 50 which is fitted into a gasket 60 receivable with a cell culture base plate 70. FIGS. 7 and 8 show the assembled relationship between the loading station assembly 2 and the cell culture plate 50. The culture plate 50 includes a base 51, a body 52 and a flexible membrane 53 sandwiched therebetween. The body 52 includes a plurality of well walls 54 which define wells 55. Floors 56 of the wells 55 are formed from the flexible membrane 53. The loading station assembly 2 is sized and configured to be positioned in an underlying relationship to the cell culture plate 50 such that the upper surfaces 24 of the flanges 18 directly support and contact an underside of the flexible cell culture membrane 53 in the location of each well 55. The entire underside of the floors 56 of the wells 55 are not covered by the flanges 18 but instead, as shown in FIG. 7, only a portion of the flexible membrane 53 is supported by the loading posts 12 beneath each well 55. Preferably, the upper surface 24 of each flange 18 is centered on the underside of each floor 56. Although the cell culture plate 50 is depicted as having circular shaped wells 55 and the upper surfaces 24 of the flanges 18 are depicted as being circular, the invention is not limited to these forms. Other geometrical configurations for all these elements may be employed.

The planar member 10 is adapted to abut against an underside of the base 51 of the cell culture plate 50. When installed with the gasket 60 and cell culture base plate 70, the planar member 10 engages with the underside of the base 51. As an example, the cell culture base plate 70 includes recessed portions 71, each being adapted to receive the gasket 60, the loading station assembly 2 and the cell culture plate 50. A bottom of each recessed portion 71 defines an opening 72. The openings 72 communicate via a passageway (not shown) defined in the base plate 70 with ports 73 and 74. Ports 73 and 74 are adapted to be connected to a vacuum or other source of negative pressure.

In operation, when negative pressure is applied to the ports 73 or 74, a vacuum is drawn through the passageway and openings 72 to the underside of the planar member 10 and through the central opening 28. The volume of space between the upper surface 22 of planar member 10 and the underside of the well floors 56 is at least partially evacuated. The flexible membrane 53 of each floor 56 is pulled in the direction of the planar member 10 as shown schematically in FIG. 8. Because the upper surfaces 24 of the flanges 18 have smaller surface areas than the surface areas of the well floors 56, only a periphery of the flexible membrane 53 within the wells 55 is pulled downwardly. In so doing, the membrane 53 is stretched in a plane across the upper surfaces 24 of the flanges 18 resulting in an equibiaxial strain on the flexible membrane 53. Cells which are adhered to the flexible membrane 53 likewise experience equibiaxial strain. The vacuum may be applied once, intermittently, regularly or in a variety of frequencies to induce equibiaxial strain on the cells over time. The chamfered portion 26 of the flange 18 provides a guide against which the flexible membrane 53 may slide as the flexible membrane 53 is pulled toward the planar member 10 thereby minimizing wear on the flexible membrane 53.

When the flexible membrane 53 is made from a transparent silicone material such a material produced by the Bisco Company under Product No. HT 6240, the loading station assembly is preferably formed from a transparent plastic material. In this manner, light is able to pass through the loading station assembly 2 and flexible membrane 53 so that cells adhering to the flexible membrane 53 are clearly visible. Additionally, such an arrangement also permits the use of a microscope therewith to view the cells while an equibiaxial strain or other strain is applied thereto since the cells remain in the same plane throughout the stretching paradigm.

Various strains or stresses on cells adhering to the flexible membrane 53 may be induced by employing loading posts having alternative geometrical shapes on their upper surfaces. For example, the plane of the upper surface may be slanted, the flange of the loading post may be frustoconical or frustopyramidal in shape or the upper surface may have single or multiple peaks. Such various geometrical shapes of the loading post flange or upper surface of the flange induce different strains and/or stresses upon the cells adhered to the flexible membrane.

Figure 10:
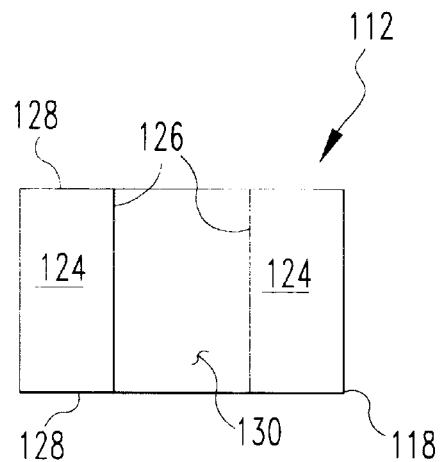
FIG. 10 is a top view of the loading post show.
Figure 9:
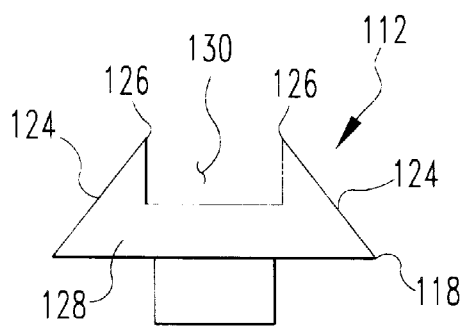
FIG. 9 is a side elevation view of a second embodiment of the loading post.
Figure 11:
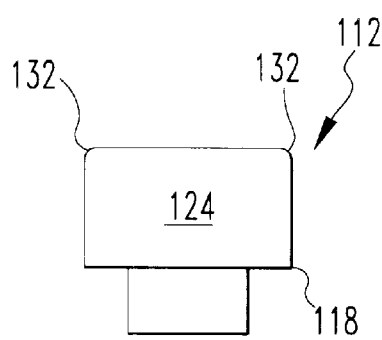
FIG. 11 is an end elevation view of the loading post shown in FIG. 9.

One such alternative loading post 112 is shown in FIGS. 9–11. The loading post 112 includes a generally rectangularly shaped flange 118 having a pair of slanted upper surfaces 124 terminating in a pair of ridges 126 and defining a groove 130 therebetween and a pair of vertical sides 128. In use with a cell culture plate having wells with bottoms formed from a flexible membrane, the membrane is stretched across the groove 130 and along the slanted upper surfaces 124. Ends 132 of the ridges 126 preferably are rounded to reduce wear on the membrane. Cells adhering to the portion of the membrane deformed over the slanted upper surfaces 124 experience strain as well as some shear stress due to movement of the cell culture fluid thereover.

Figure 12:
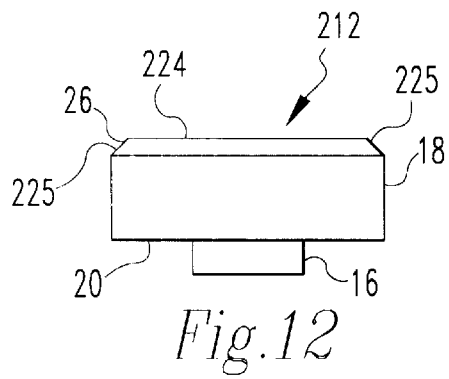
FIG. 12 is a side elevation view of a third embodiment of the loading post.
Figure 13:
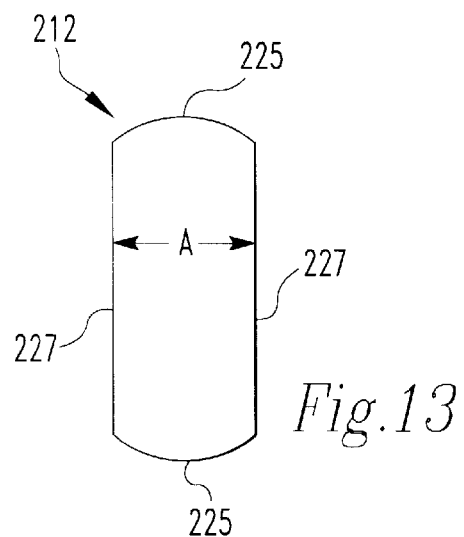
FIG. 13 is a top view of the loading post shown in FIG. 12.
Figure 14:
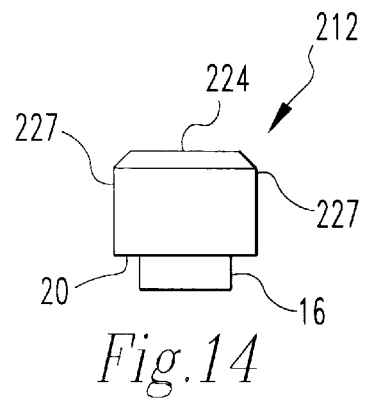
FIG. 14 is an end elevation view of the loading post shown in FIG. 12.

Another alternative loading post 212, shown in FIGS. 12–14, allows for uniaxial stretching of the membrane to induce uniaxial strain on cells attached thereto. The loading post 212 has an upper surface 224 with a length which is sized and configured to completely support the underside of the membrane 53 in one direction only. Ends 225 of the upper surface 224 are rounded to conform with the circular shape of the underside of the floor 56 of the well 55. The distance between the ends 225 is approximately equal to the diameter of the opening of the well 55, and the length of the upper surface 224 between the ends 225 is greater than the width of the upper surface 224 between sides 227. In use, the membrane 53 is pulled downwardly under vacuum across the sides 227 of the upper surface 224. The membrane 53 is not pulled downwardly over the ends 225 but is stretched generally only in the direction of the arrow A shown in FIG. 13 so that uniaxial strain in the direction of arrow A is experienced by cells attached to the membrane 53. The width of the upper surface 224 can be varied according to the particular stretching paradigm desired. The loading post 212 may be rotated within the aperture 14 to induce uniaxial strain in various directions. For example, the loading post 212 may be used in uniaxially stretching a membrane 53 with cells attached thereto in a first direction. The loading post 212 may then be rotated by a preselected amount, e.g., 90°, and used in uniaxially stretching the membrane 53 again. The cells will have experienced strain in a pair of perpendicular directions.

The loading posts 12, 112 and 212 of the loading station assembly are interchangeable such that the loading posts positioned on the planar member 10 may have the same or different upper surface profiles. In addition, one or more of the apertures 14 may be vacant such that the membrane positioned thereover is permitted to flex arcuately when negative pressure is applied thereto. Alternatively, the surface area of the upper surface 24 of the flange 18 may be the same as the surface area of the well floor 56 such that negative pressure applied to the loading post 12 does not impact the flexible membrane 53 in the corresponding well 55 and the flexible membrane 53 is stationary. The cells adhering to the stationary flexible membrane 53 may be compared to cells which are actively strained. In such a manner, varying stresses and strains may be applied to cells cultured in different wells of the same cell culture plate by altering the configuration or presence of the upper surface of the loading post. The various geometric shapes of the loading posts may be used so that one membrane of one well in the culture plate is deformed over one type of loading post and then a different loading post is used for the same well. This effect can be achieved by rotating the loading posts from one position to another on the planar member.

In an alternative embodiment (not shown), the height of the loading post may be adjustable. For example, the loading post flange may be formed in two parts. An upper part includes an upper portion having an upper horizontal surface and a lower portion having a lower surface angled at about 45° to vertical. The angled lower surface mates with a lower part having a complementary angled upper surface. The upper and lower parts are positioned adjacent to each other along their complementary angled surfaces. The position of the upper part relative to the lower part determines the overall height of this loading post.

In another embodiment of the loading station assembly (not shown), an adjustable pin such as a screw or the like is received within the aperture 14 and is upwardly and downwardly moveable. The pin extends into the aperture and is positioned adjacent the loading post column. By moving the pin up or down, the post column is likewise upwardly or downwardly positionable.

Alternatively, a central plunger may be received within a central area of the column and is upwardly and downwardly extendable through the aperture in the loading post upper surface. By moving the plunger to various positions, the geometrical profile of the loading post against which the membrane bears may be altered. Likewise, a sleeve may surround the loading post and is upwardly and downwardly movable to change the profile of the loading post.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

I claim:

1. A loading station assembly for allowing stretching of a flexible cell culture membrane, said assembly comprising:
  a planar member and a post extending from a surface of said planar member, an upper surface of said post being configured to support a flexible cell culture membrane, said planar member defining a passageway configured to allow fluid to flow through from one side of said planar member to an opposite side of said planar member,
  wherein said flexible cell culture membrane is stretchable at a periphery of said upper surface toward said planar member.

2. The loading station assembly as claimed in claim 1 wherein said planar member defines an aperture and said post is removably received within said aperture such that when said post is removed, the cell membrane is unrestricted from flexing downwardly.

3. The loading station assembly as claimed in claim 2 wherein said planar member defines a plurality of apertures and said assembly further comprises a plurality of posts, each said post having an upper surface configured to support a flexible cell culture membrane and being removably received within one of said apertures.

4. The loading station assembly as claimed in claim 3 wherein each said post comprises a body receivable within one of said apertures and a flange including said upper surface, said flange being positionable against said planar member.

5. The loading station assembly as claimed in claim 1 wherein said upper surface is configured to allow for equibiaxial stretching of a membrane.

6. The loading station assembly as claimed in claim 5 wherein said upper surface is substantially circular.

7. The loading station assembly as claimed in claim 1 wherein said upper surface is configured to allow for uniaxial stretching of a membrane.

8. The loading station assembly as claimed in claim 7 wherein the length of said upper surface is longer than the width of said upper surface.

9. The loading station assembly as claimed in claim 1 wherein said upper surface is formed in a plurality of planes.

10. The loading station assembly as claimed in claim 1 wherein said assembly is made from a transparent material.

11. A cell culture plate assembly comprising:
  a cell culture plate defining an opening and a flexible cell culture membrane covering said opening; and
  a loading station assembly positioned adjacent said cell culture plate, said loading station assembly comprising a planar member and a post extending from a surface of said planar member, an upper surface of said post supporting a portion of said flexible membrane covering said opening, said planar member defining a passageway configured to allow fluid to flow through from one side of said planar member to an opposite side of said planar member,
  wherein said flexible membrane is stretchable at a periphery of said upper surface toward said planar member.

12. The cell culture plate assembly as claimed in claim 11 wherein said planar member defines an aperture and said post is removably received within said aperture such that when said post is removed, said cell culture membrane is unrestricted from flexing downwardly.

13. The cell culture plate assembly as claimed in claim 11 wherein said cell culture plate defines a plurality of openings, each said opening covered by said cell culture membrane and said planar member defines a plurality of apertures and said assembly further comprises a plurality of posts, each said post supporting a portion of said cell culture membrane covering one of said openings and being removably received within one of said apertures.

14. The cell culture plate assembly as claimed in claim 13 wherein each said post comprises a body receivable within one of said apertures and a flange including said upper surface, said flanges being positionable against said planar member.

15. The cell culture plate assembly as claimed in claim 11 wherein said upper surface is configured to allow for equibiaxial stretching of a membrane.

16. The cell culture plate assembly as claimed in claim 15 wherein said upper surface is substantially circular.

17. The cell culture plate assembly as claimed in claim 11 wherein said upper surface is configured to allow for uniaxial stretching of a membrane.

18. The cell culture plate assembly as claimed in claim 17 wherein a dimension of said upper surface is approximately equal to a dimension of said opening.

19. The cell culture plate assembly as claimed in claim 18 wherein said opening is substantially circular and the length of said upper surface is approximately equal to the diameter of said opening and the width of said upper surface is less than the diameter of said opening.

20. The cell culture plate assembly as claimed in claim 11 wherein said upper surface is formed in a plurality of planes.

21. The cell culture plate assembly as claimed in claim 11 wherein each of said flexible membrane and said loading station assembly is made from a transparent material.

22. The cell culture plate assembly as claimed in claim 11 wherein said post upper surface supports all of said flexible membrane covering said opening.

* * * * *